United States Patent [19]
Nath et al.

[11] Patent Number: 5,886,263
[45] Date of Patent: Mar. 23, 1999

[54] METHOD OF RESONANT LIFE CYCLE COMPARISON INSPECTION AND TESTING

[75] Inventors: Robert H. Nath; James J. Schwarz, both of Albuquerque; Jay G. Saxton, Corrales, all of N. Mex.

[73] Assignee: Quatrosonics, Albuquerque, N. Mex.

[21] Appl. No.: 826,149

[22] Filed: Mar. 27, 1997

[51] Int. Cl.⁶ .............................. G01N 29/12; G06G 7/68
[52] U.S. Cl. .......................... 73/579; 364/150; 364/151; 702/36
[58] Field of Search .............................. 73/579, 602, 587, 73/594, 592, 659, 660; 364/507, 508, 150, 151

[56] References Cited

U.S. PATENT DOCUMENTS

| 4,799,387 | 1/1989 | Matsuo | 73/620 |
| 4,984,173 | 1/1991 | Imam et al. | 364/508 |
| 5,327,358 | 7/1994 | Stubbs | 364/507 |
| 5,493,511 | 2/1996 | Wincheski et al. | 364/508 |
| 5,533,399 | 7/1996 | Gibson et al. | 73/579 |
| 5,686,667 | 11/1997 | McCollum et al. | 73/579 |

*Primary Examiner*—Hezron Williams
*Assistant Examiner*—Rose M. Miller
*Attorney, Agent, or Firm*—Ronald R. Snider

[57] ABSTRACT

A method of resonant ultrasonic measurement frequencies to determine materials properties is combined with the use of a finite element model and empirical data made from an actual prototype part to create a validated finite element model. The validated finite element model is then used as a standard for comparison to additional production parts, and production part measurement data is stored and archived by part serial number for future comparison to part tests performed during periodic maintenance of equipment utilizing the part after shipment to customer.

7 Claims, 1 Drawing Sheet

METHOD OF RESONANT LIFE CYCLE COMPARISON INSPECTION AND TESTING

BACKGROUND OF THE INVENTION:

1. Field of the Invention

This invention relates to the field of resonant ultrasound spectroscopy (RUS) and more particularly to the use of RUS for correcting or validating finite element models; developing initial testing criteria; initial testing of production parts; and use of archival resonant frequency records for subsequent testing of parts during maintenance procedures.

2. The Prior Art

Resonant ultrasound testing is known in the prior art as exemplified by U.S. Pat. Nos. 4,976,148 Migliori et al., 5,062,296 Migliori et al., 5,351,543 Migliori et al., 5,355,731 Dixon et al., 5,495,763 Rhodes et al., 5,408,880 Rhodes et al., and 5,425,272 Rhodes et al.

U.S. Pat. No. 5,355,731 teaches measurement of sphericity utilizing resonant ultrasound spectroscopy. In this disclosure, a first set of calculations are used to determine resonant frequencies as the functions of Poisson's ratio where the spherical objects have an ideal dimension. Next, calculations are made to determine a set of resonant frequencies where there is a deviation from dimensions of the ideal object dimensions. Then a production object is measured by resonant ultrasound (RUS), and is compared to the calculated values to determine the deviation from the ideal object dimensions.

Migliori U.S. Pat. No. 4,976,148 teaches the use of resonant ultrasound spectroscopy (RUS) for determination of elastic constants of a sample.

BRIEF SUMMARY OF THE INVENTION

The prior art includes strain gauge devices embedded in parts which can indicate deformation when compared to historical baseline data. This can indicate that the metal had been deformed or yielded. It can also measure a strain, and if measurements are made while the structure is being stressed in a precise quantitative manner and it will permit the inference of a change in modules due to fatigue, overload, heat damage, or some other factor. In other words, hooking up a resistance measurement instrument to a landing gear with a built-in strain gauge will tell only if the metal has already yielded, i.e., permanently stretched. This is considered to be a metal failure unless there is a known load change placed upon the assembly.

In this invention, Applicant provides for a complete method for resonant inspection for periodic maintenance which encompasses the entire life of a product. Applicant initially provides for materials testing by resonant ultrasound to provide data on material elastic properties, use of these material elastic properties to permit creation of a finite element model (FEM) of a part based upon part geometry and these material properties, prediction of resonant modes based upon the finite element, measurement of resonant mode frequencies of a prototype to obtain empirical data, adjustment of the finite element model to match the empirical data and to provide a validated finite element model (VFEM), measurement of resonant mode frequencies of at least one production part upon completion of manufacture of a production part, comparison of resonant mode frequencies of at least one production part to a validated finite element model (VFEM) to obtain comparative data, and subsequent inspecting of the at least one production part at maintenance intervals by comparing its resonant mode frequencies found during maintenance to comparative data recorded in memory at the time the part was produced. The inspection results are added to the archived record for that serial number part, at each inspection intrval.

This invention is particularly advantageous for use in testing components of high value and significant consequences in the event of a failure such as aircraft turbine rotors and disks, both upon initial manufacture, and for subsequent maintenance. The use of resonant ultrasound spectroscopy (RUS) detection of flaws at periodic maintenance intervals as they develop in the components during the intervening periods of operation can be accomplished. It is possible to detect stress failures and metal structure precursors to cracks in parts which may occur internally even prior to the development of internal or external cracks. This technique, therefore, leads to detection of potentially catastrophic failures in aircraft rotors and disks long before such failure may occur, or before it can be detected by other non-destructive means. This method also provides an archived record of objective measurements relating to the structural integrity of the component at the time of the inspection.

DETAILED DESCRIPTION

Figure 1:
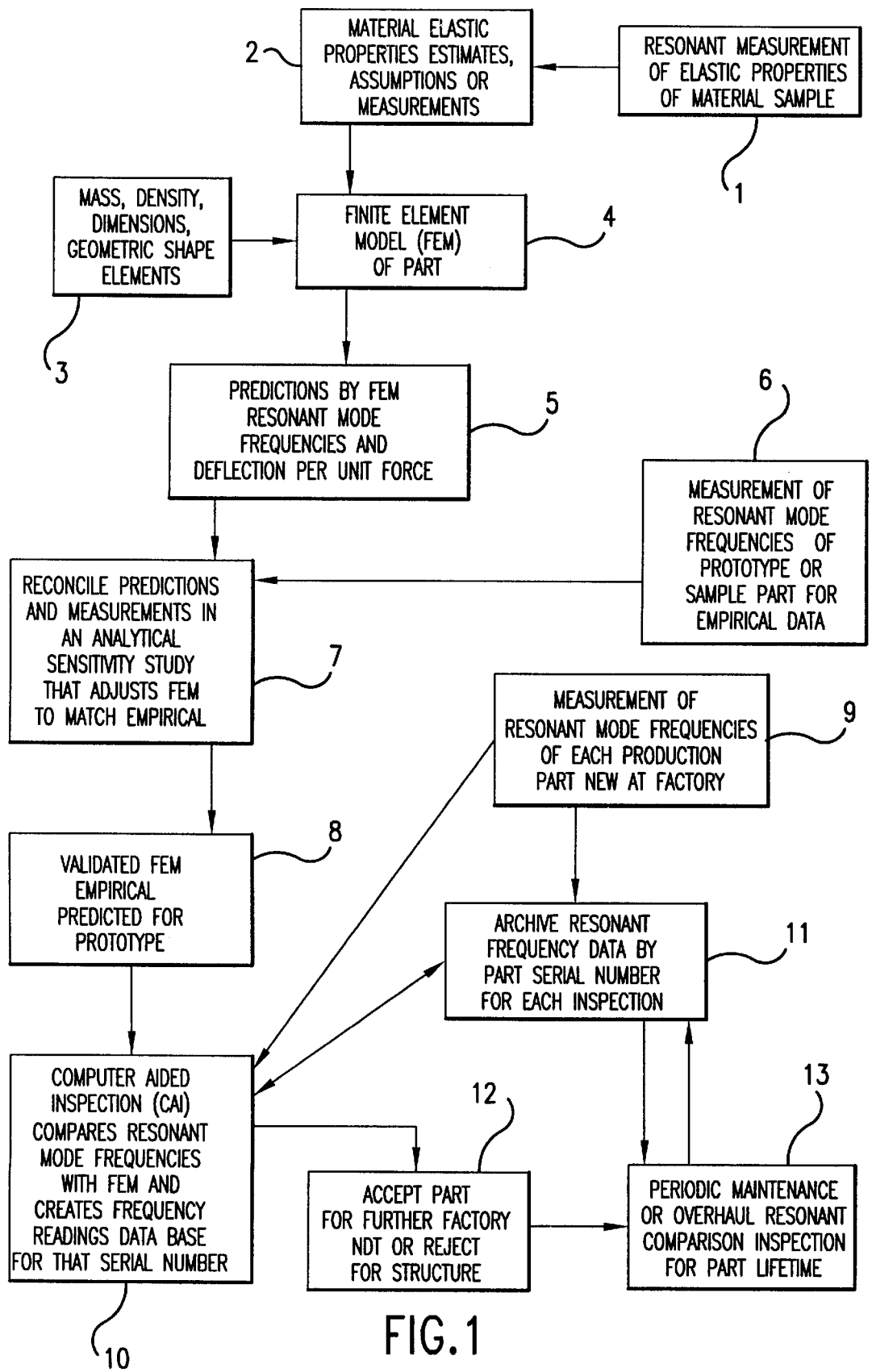
FIG. 1 shows a block diagram of the steps of the method of this invention.

FIG. 1 shows in block form the steps of this invention.

The first step in this process is the use of resonance to measure the elastic properties of samples of an actual raw material to be used in an end product. This testing may occur at ambient temperatures or at temperatures for which it is anticipated that the part will operate. This data provides an input database to complement published material relating to material elastic properties. As shown in FIG. 1, resonant measurement of elastic properties of the sample material as a step in the process is designated by Block 1. Resonant measurement of the sample may be in accordance with the teachings of U.S. Pat. No. 4,976,148; the teachings of "Resonant ultrasound spectroscopic techniques for measurement of the elastic moduli of solids," by A. Migliori et al., *Physica B*, published by North-Holland Physics publication of a paper received 20 Oct. 1992; and the teachings of "Resonant ultrasound spectroscopy," by Julian Maynard, American Institute of Physics, 1996, all of which are incorporated herein by reference.

Next, comparison with known elastic properties along with estimates assumptions, etc. occurs in Block 2.

Once the material elastic properties are determined, a finite element model (FEM) of the part is then mathematically determined. This finite element model is based upon mass, density, part dimensions, geometrical shape, as well as the material elastic properties which were determined in Blocks 2 and 3. The finite element model (mathematical) of the part is then created and is generally depicted as in Block 4.

As shown in Block 5, predictions are then made of resonant mode frequencies and deflection per unit force are then made based upon the finite element model of Block 4.

The next step is then measurement of the resonant mode frequencies of a prototype or sample part to obtain empirical data for a part. Obviously, this part should be one which has been verified to be an accurate prototype both in dimensions and material properties.

As shown in Block 7, the predictions and measurements made in Block 5 are then compared to the empirical data obtained by actual measurement of a prototype from Block 6 to reconcile the measurements and analytical sensitivity. This step is depicted in Block 7.

A validated finite element model (validated by empirical data) is then generated where the resonant modes are predicted for the prototype and for subsequent production use (Block 8).

As shown in Block 9, resonant mode frequencies are then obtained for each production part when new at the point of manufacture. This data is then provided to Block 10 which indicates that the computer-aided inspection (CAI) is used to compare the resonant mode frequencies with the finite element model to confirm the structural characteristics of the new part and also to create a frequency reading database for the particular serial number of the part produced.

The data created in Block 10 is then used to create an archival record (Block 11) of resonant frequency data by part serial number.

In Block 12, there is shown a step wherein the part is accepted for further part non-destructive testing or rejected for structural failure to pass inspection.

In Block 13, there is shown the after manufacture periodic inspection of the part wherein overhaul includes resonant inspection. The overhaul resonant inspection results are compared to the archival resonant frequency data which is in turn based upon the original part inspection at the factory, and any interim maintenance inspection.

The resonant maintenance comparison step (13) will signal any significant change in a part such as a turbine rotor. These changes can include cracks or growth of small internal material flaws, heat-caused changes in material either general or localized, fatigue-induced changes in material even before cracks appear, and impact damaged area if the damage causes local anistropey not present in the rotor when the rotor baseline was first measured upon manufacture.

The archival resonant frequency data can also be analyzed to determine trends in part performance, i.e., long degradation of the part over a period of time.

The use of resonant testing and verification based upon validated models allows reduction of time in production, reduced costs of design and manufacture and provides improved design-based quality.

PERMANENT ATTACHMENT OF TRANSDUCERS

In part manufacture, archival data recording, and subsequent maintenance testing, it may be desirable to utilize piezoelectric crystals (with backloading) which are permanently attached to parts which are undergoing periodic maintenance inspection. The use of permanently attached piezoelectric crystals provides for repeat measurement at exactly the same location under the same conditions, and hence eliminates any variables that may be associated with crystal attachment or measurement location on the part. Still further, crystal permanent attachment allows measurement at part locations which may not be readily accessible once a part is installed in a larger assembly such as an aircraft.

Part structure, with small permanently attached piezoelectric crystals, can be mechanically excited through a sweep of frequencies by a portable vibration source controlled by test instruments as described above. The piezoelectric crystals with backloads weigh only a few ounces per one hundred and the material costs for such crystals is only in the order of $20.00 per hundred. Resonant frequency measurements with this type of crystal are generally in excess of 1 Kh.

Because this type of permanently attached piezoelectric crystal can be added after an aircraft is built, it can be applied to all of the aircraft parts. Still further, the after-built feature allows retrofitting on current commercial and military fleets. For new aircraft, there is also no need to requalify existing materials for aircraft construction to allow for unknown effects of the internal incorporation of foreign objects such as sensors. If the material already has embedded into it or attached to it, piezoelectric sensors and actuators, these are taken into consideration in all subsequent measurements.

In an aircraft critical part such as landing gear, up to 100 safety critical locations may be selected and 100 permanently attached piezoelectric crystals can be attached thereto which will permit a verification of the unchanged condition of the assembled and thus constrained components of a landing gear assembly when compared to baseline resonance patterns recorded and archived at a time that the assembly had been certified as acceptable. A similar approach can be used for a wing spar or longeron inspection.

This measurement technique permits better identification of resonant modes because the effect on changes in amplitude base on transducer location is minimized relative to the standing wave location. This, in turn, permits concentration on analysis of higher order amplitude signals from each crystal which will emphasis the influence of local structure on local resonance of a complex assembly. This, in turn, greatly simplifies the resonance spectrum and gives information by location on any deterioration of the component being measured.

What is claimed:

1. A method for resonant inspection for resonant maintenance comparison comprising the steps of:

creating a finite element model (FEM) of a part to be inspected wherein said model is based upon part geometry and material properties;

predicting resonant mode frequencies based upon said finite element model (FEM);

measuring of resonant mode frequencies of a prototype part to obtain empirical data;

adjusting the finite element model (FEM) to match said empirical data to provide a validated finite element model (VFEM);

measuring of resonant mode frequencies of at least one production part upon completion of manufacture of said production part;

comparing said resonant mode frequencies of said at least one production part to said validated finite element model (VFEM) to obtain comparative data;

storing in an archival memory said comparative data; and inspecting said at least one production part at maintenance intervals by comparing the production part resonant mode frequencies to said comparative data.

2. The method in accordance with claim 1 further comprising the step of resonant measuring of elastic properties of a material sample of material used to manufacture said prototype part.

3. The method in accordance with claim 2 further comprising the step of determination of material elastic properties based upon said resonant mode measurement of elastic properties of said material sample and estimates and additional assumptions.

4. The method in accordance with claim 1 wherein said finite element model (FEM) of said production part is determined by mathematically modeling the part as a function of resonant measurement of elastic properties of a material sample: mass, density, and part shape.

5. The method in accordance with claim 1 further comprising the step of accepting of said at least one Production part for further factory non-destructive testing, or rejecting said at least one production part because of excessive deviation from said validated finite element model (VFEM).

6. The method in accordance with claim 1 further comprising the steps of:

performing periodic maintenance and overhaul during which resonant ultrasound spectroscopy frequency (RUS) comparison inspection is carried out; and comparing said overhaul resonant inspection to said stored part archival resonant inspection comparative data to determine if there has been a change in the part.

7. The method in accordance with claim 1 wherein the steps of measuring at least one production part resonant mode frequency includes permanently attaching measurement transducers.

* * * * *